(12) United States Patent
Rahm et al.

(10) Patent No.: US 6,307,086 B1
(45) Date of Patent: Oct. 23, 2001

(54) METHOD FOR PRODUCING LONG-CHAIN GLYCINE-N,N-DIACETIC ACID DERIVATIVES

(75) Inventors: Rainer Rahm, Ludwigshafen; Thomas Greindl; Alfred Oftring, both of Bad Duerkheim; Guenter Oetter, Frankenthal; Juergen Detering, Limburgerhof; Gerold Braun, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/463,998

(22) PCT Filed: Aug. 17, 1998

(86) PCT No.: PCT/EP98/05220

§ 371 Date: Mar. 21, 2000

§ 102(e) Date: Mar. 21, 2000

(87) PCT Pub. No.: WO99/10314

PCT Pub. Date: Mar. 4, 1999

(30) Foreign Application Priority Data

Aug. 21, 1997 (DE) .............................. 197 36 476

(51) Int. Cl.$^7$ .................................. C07C 253/00

(52) U.S. Cl. .......................... 558/371; 558/372

(58) Field of Search ..................... 558/371, 372

(56) References Cited

U.S. PATENT DOCUMENTS

| | | | |
|---|---|---|---|
| 5,817,864 | * 10/1998 | Greindl et al. | 560/171 |
| 5,849,950 | * 12/1998 | Greindl et al. | 562/571 |
| 6,005,141 | * 12/1999 | Schneider et al. | 562/571 |

FOREIGN PATENT DOCUMENTS 0 745 582   12/1996  (EP) .

(List continued on next page.)

OTHER PUBLICATIONS

Hiroyuki Minamikawa, et al.: "Asymmetric Hydrocyanation (List continued on next page.)

*Primary Examiner*—Fiona T. Powers
(74) *Attorney, Agent, or Firm*—Oblon, Spivak, McClelland, Maier & Neustadt, P.C.

(57) ABSTRACT

A process for preparing compounds of the formula IIb (IIb)

Figure 1:
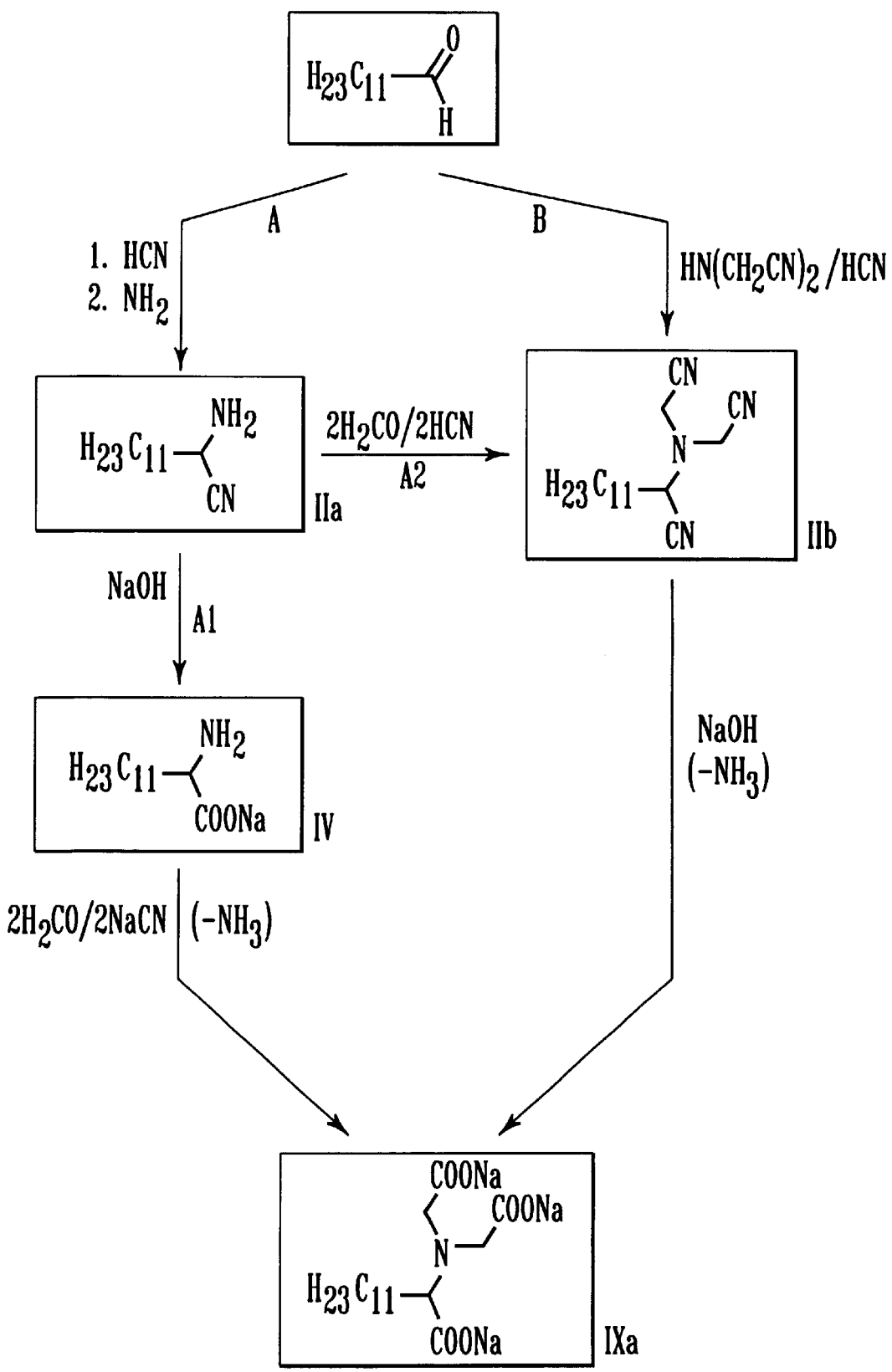

where R is $C_6$–$C_{30}$-alkyl or $C_6$–$C_{30}$-alkenyl, which may additionally have upto 5 hydroxyl groups, formyl groups, $C_1$–$C_4$-alkoxy groups, phenoxy groups or $C_1$–$C_4$-alkoxycarbonyl groups as substituents and may be interrupted by upto 5 nonadjacent oxygen atoms, or alkoxylate groups of the formula —$(CH_2)_k$—O—$(A^1O)_m$—$(A^2O)_n$—Y where $A^1$ and $A^2$ are, independently of one another, 1,2-alkylene groups having 2 to 4 carbon atoms, Y is hydrogen, $C_1$–$C_{12}$-alkyl, phenyl or $C_1$–$C_4$-alkoxycarbonyl, and k is 1, 2 or 3, and m and n are each numbers from 0 to 50, and the total of m+n must be at least 4, by reacting iminodiacetonitrile with aldehydes of the formula R—CHO and HCN or alkali metal cyanides, the process being carried out a) in the absence of an organic solvent and in the presence of a Lewis or Brönsted acid, or
b) in the presence or absence of an organic solvent and in the presence of an emulsifier, or
c) in the presence or absence of an organic solvent and under a pressure in the range from 1 to 40 bar.

2 Claims, 2 Drawing Sheets

FOREIGN PATENT DOCUMENTS 195 18 986
    A1   12/1996  (DE).

195 18 987
    A1   12/1996  (DE).

94/29421   12/1994  (WO).

OTHER PUBLICATIONS of Aldehydes Using Chiral Titanium Reagents" XP–002100390: Bull. Chem. Soc. Japan, 61, Pages 4379–4383, 1988.

Chemical Abstracts, Columbus, Ohio, US, XP–002100391, Page 270, Abstract No. 70:46856, Michio Nakanishi et al. "Higher Unsaturated Aliphatic Amino Acids", 1969.

* cited by examiner

METHOD FOR PRODUCING LONG-CHAIN GLYCINE-N,N-DIACETIC ACID DERIVATIVES

The invention relates to a process for preparing long-chain glycine-N,N-diacetic acid derivatives.

Glycine-N,N-diacetic acid derivatives can be employed as biodegradable completing agents for alkali metal and heavy metal ions.

Various processes for preparing these compounds are known.

WO 94/29421 describes processes for preparing glycine-N,N-diacetic acid derivatives. These entail converting long-chain aliphatic aldehydes with iminodiacetonitrile and HCN It is an object of the present invention to provide a process for preparing glycine-N,N-diacetic acid derivatives by reacting iminodiacetonitrile with aldehydes and HCN or alkali metal cyanides, which avoids the abovementioned disadvantages and is suitable for transfer to the industrial scale. The process ought to give high yields in short reaction times; it is additionally intended to provide alternative processes which avoid the abovementioned disadvantages.

We have found that this object is achieved by processes with several variants as described below by means of component steps. The glycine-N,N-diacetic acid derivatives can be obtained, for example, by reactions shown in the two reaction schemes detailed below.

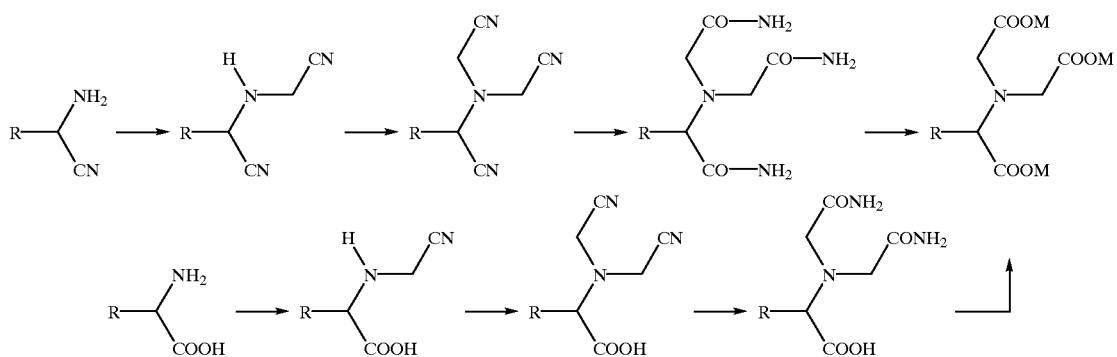

alkylglycinonitrile-N,N-diacetonitrile, the resulting compound being hydrolyzed. The compounds can likewise be obtained by reacting the aldehydes with HCN and ammonia to give substituted amino nitrites, which are hydrolyzed to substituted amino acids, which is followed by reaction with formaldehyde and sodium cyanide. The process is too complicated for some compounds because long reaction times are necessary. Moreover the yields of the required compounds are still in need of improvement. The proposed processes are not always suitable for transfer to the industrial scale.

DE-A 195 18 986 describes a process for preparing gly-cine-N,N-diacetic acid derivatives by reacting glycine derivatives or their precursors with formaldehyde and hydrogen cyanide or reacting iminodiacetonitrile or iminodiacetic acid with appropriate aldehydes and hydrogen cyanide in aqueous acidic medium. The starting material employed in this case is the unpurified crude material derived from the industrial synthesis of glycine derivatives or their precursors or of iminodiacetonitrile or iminodiacetic acid, or mother liquors produced in syntheses of these types. The process is carried out as indicated in WO 94/29421.

DE-A-195 18 187 relates to a process for preparing glycine-N,N-diacetic acid derivatives by reacting glycine derivatives or their precursors with formaldehyde and alkali metal cyanide in aqueous alkali medium. The process is likewise based on the process described in WO 94/29421, but firstly from 0.5 to 30% of the amount of alkali metal cyanide required for the reaction is added to the glycine derivatives or their precursors, and then the remaining amount of alkali metal cyanide and the formaldehyde are metered in simultaneously over a period of from 0.5 to 12 hours. Even this variant of the process cannot eliminate all the abovementioned disadvantages.

Figure 2:
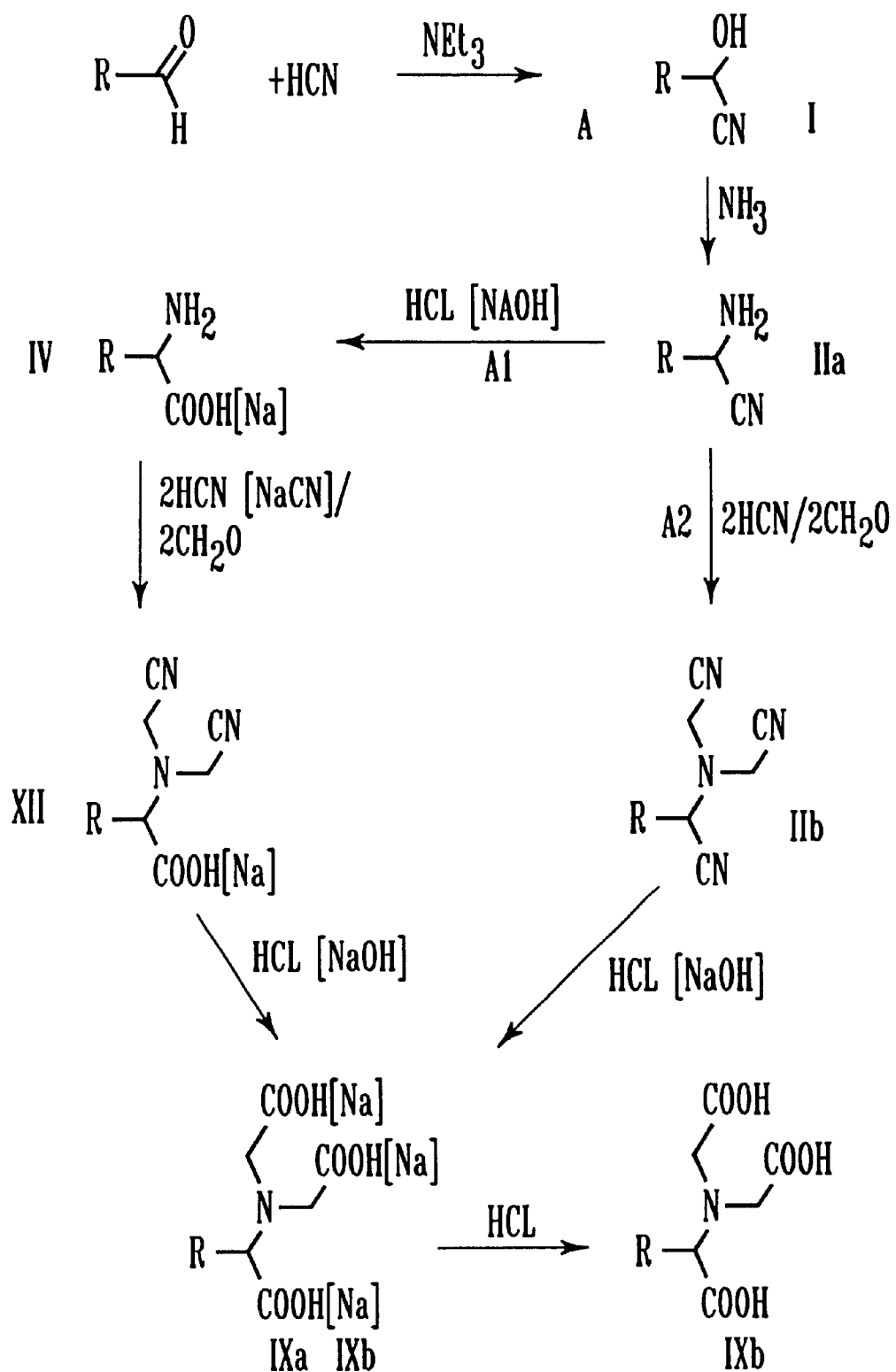

The processes according to the invention are additionally explained by means of the reaction schemes depicted in the drawing, where FIG. 1 shows reaction schemes A and B based on dode-canal as example and FIG. 2 shows reactions schemes A1 and A2 for aldehydes of the formula R—CHO, where R has the meaning indicated hereinafter. The object is achieved in particular by a process for preparing compounds of the formula IIb

(IIb)

where R is $C_6$–$C_{30}$-alkyl or $C_6$–$C_{30}$-alkenyl, which may additionally have upto 5 hydroxyl groups, formyl groups, $C_1$–$C_4$-alkoxy groups, phenoxy groups or $C_1$–$C_4$-alkoxycarbonyl groups as substituents and may be interrupted by upto 5 nonadjacent oxygen atoms, or alkoxylate groups of the formula —$(CH_2)_k$—O—$(A^1O)_m$—$(A^2O)_n$—Y where $A^1$ and $A^2$ are, independently of one another, 1,2-alkylene groups having 2 to 4 carbon atoms, Y is hydrogen, $C_1$–$C_{12}$-alkyl, phenyl or $C_1$–$C_4$-alkoxycarbonyl, and k is 1, 2 or 3, and m and n are each numbers from 0 to 50, and the total of m+n must be at least 4, by reacting iminodiacetonitrile with aldehydes of the formula R—CHO and HCN or alkali metal cyanides, the process being carried out a) in the absence of an organic solvent and in the presence of a Lewis or Brönsted acid, or b) in the presence or absence of an organic solvent and in the presence of an emulsifier, or c) in the presence or absence of an organic solvent and under a pressure in the range from 1 to 40 bar.

It has been found according to the invention that is reactions with aldehydes and HCN or alkali cyanides, as well as the hydrolysis of nitriles or amides to acids, can be speeded up and, moreover, the yield is increased under an elevated pressure in the range from 1 to 40 bar, preferably from 1.5 to 30 bar, in particular from 2 to 15 bar. These preferred pressure ranges also relate to the other reactions mentioned. Reaction of iminodiacetonitrile with aldehydes and HCN can moreover be speeded up by reacting in the absence of an organic solvent and, in particular, in the absence of further water in the reaction system, ie. by reacting without diluent and in the presence of a Lewis or Brönsted acid.

The reaction can additionally be carried out in the presence of an emulsifier, which is preferably employed in a concentration of from 1 to 50 g/l, particularly preferably 2 to 30 g/l of reaction mixture. Emulsifiers which can be employed are all compounds suitable for this purpose. Examples are anionic, cationic, amphoteric and nonionic emulsifiers. The lipophilic end groups of the emulsifiers are, as a rule, straight-chain or branched alkyl radicals which may contain unsaturated bonds, aryl radicals or alkylaryl radicals. Examples of suitable hydrophilic end groups for anionic emulsifiers are carboxylate, sulfonate, sulfate, phosphate, polyphosphate, lactate, citrate and tartrate. Suitable examples of cationic emulsifiers are amine salts and quaternary ammonium compounds. Suitable amphoteric emulsifiers are zwitterionic compounds of the amino acid type and, for example, betaine. Suitable for nonionic emulsifiers are residues of alcohols, polyethers, glcyerol, sorbitol, pentaerythritol, sucrose, acidic acid or lactic acid. The emulsifiers may additionally have hydrophilic groups in between such as hydroxyl, ester, sulfamide, amide, polyamide, polyamine, amine, ether, polyether, glycerol, sorbitol, pentaerythritol or sucrose groups.

Examples of suitable emulsifiers are ethoxylation products and fatty acid condensation products, fatty alcohol ethoxylates and, where appropriate, polyglycols and products of the reaction of phenols and oils with ethylene oxide.

The emulsifiers particularly employed are compounds such as alkali metal alkyl sulfates, in particular sodium dodecyl sulfate or mixtures of hydrophobic alkyl sulfates. It is also possible to employ nonionic surfactants such as fatty alcohol ethoxylates, which are, in particular, low-foaming.

The process step indicated above relates to process B for converting the initial aldehyde into the compound of the formula IIb.

The invention also relates to a process for preparing compounds of the formula IIa

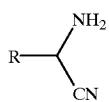
(IIa)

where R has the abovementioned meaning, by reacting aldehydes of the formula R—CHO with HCN or alkali metal cyanides and ammonia in the presence of an organic base, the reaction being carried out under a pressure in the range from 1 to 40 bar. In FIG. 1, this reaction corresponds to the conversion of the initial aldehyde into the compound of the formula IIa.

The invention likewise relates to a process for preparing compounds of the formula IIb as defined above, by reacting compounds of the formula IIa as are defined above and can be prepared by the above process, with formaldehyde and HCN or alkali metal cyanides, the process being carried out in the presence or absence of a solvent under a pressure in the range from 1 to 40 bar. This reaction corresponds to the step for converting the compound of the formula IIa into the compound of the formula IIb in FIG. 1.

The invention furthermore relates to a process for preparing compounds of the formula IX

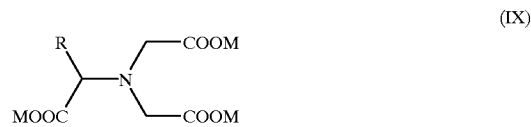
(IX)

where R has the abovementioned meaning, and M is hydrogen, alkali metal, alkaline earth metal, ammonium or substituted ammonium in the appropriately stoichiometric amounts, by reacting compounds of the formula IIb as are defined above and can be prepared by an above process, with alkali metal hydroxide solutions with or without solutions which contain ions of M, the reaction with the alkali metal hydroxide solutions being carried out under a pressure in the range from 1 to 40 bar. This reaction corresponds to the process step from the compound of the formula IIb to the compound of the formula IXa in FIG. 1.

The invention further relates to a process for preparing compounds of the formula IV

(IV)

where R and M have the abovementioned meanings, by reacting compounds of the formula IIa as are defined above and can be prepared by the above process, with sodium hydroxide solution, alkali metal hydroxide solutions and, where appropriate, solutions which contain ions of M, in the additional presence of aliphatic $C_{3-9}$ ketones, the reaction being carried out under a pressure in the range from 1 to 40 bar. This reaction step corresponds to the step for converting the compound of the formula IIa to the compound of the formula IV in FIGS. 1 and 2.

The invention additionally relates to a process for preparing compounds of the formula IX as defined above, by reacting compounds of the formula IV as are defined above and can be prepared by the above process, with formaldehyde and HCN or alkali metal cyanide and subsequent reaction with alkali metal hydroxide solutions and reaction with solutions which contain ions of M, the reactions being carried out under a pressure in the range from 1 to 40 bar. This reaction step is a step in FIGS. 1 and 2 from the compound of the formula IV to the compound of the formula IXa. Compounds of the formula IV can also be obtained by acidic or alkaline hydrolysis of hydantoins of the formula V

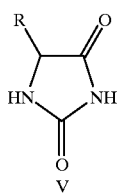

(V)

where R has the abovementioned meaning, it being possible to obtain the hydantoins by reacting, under atmospheric or superatmospheric pressure, aldehydes of the formula R—CHO with alkali metal cyanides and ammonium carbonate.

Besides the two process variants A and B (specific), the invention also relates to the following process variants B (general) C and D. In this connection, the invention relates to a process for preparing compounds of the formula IX as defined above by reacting (B) iminodiacetic acid compounds of the formula XI $$X-CH_2-NH-CH_2-Y \quad (XI)$$

where X and Y are, independently, $CO_2M$, $CO_2R^1$
where $R^1=C_{1-12}$-alkyl, $CONH_2$ or CN,
(a) with aldehydes of the formula R—CHO and HCN or alkali metal cyanides, or
(b) with cyanohydrins of the formula R—CH(OH)CN, in the presence of absence of an organic solvent under a pressure in the range from 1 to 40 bar, or
(C) glycine with aldehydes of the formula R—CHO and HCN or alkali metal cyanides with monosubstitution and subsequently with
(a) formaldehyde and HCN or alkali metal cyanides or
(b) HO—CH_2—CN
in the presence or absence of an organic solvent, it being possible to carry out the reaction under a pressure of from 1 to 40 bar, or
(D) glycine with
(a) formaldehyde and HCN or alkali metal cyanide, or
(b) HO—CH_2—CN,
with monosubstitution and subsequently with aldehydes of the formula R—CHO and HCN or alkali metal cyanide in the presence or absence of an organic solvent, it being possible to carry out the reaction under a pressure of from 1 to 40 bar,
where R in each case has the abovementioned meaning, possibly followed by a hydrolysis of nitrile or amide functionalities which are present, which can be carried out under a pressure of from 1 to 40 bar.

Process variant C complies with the following scheme:

Reaction sequence D complies with the following scheme:

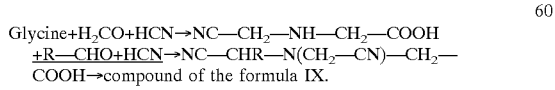

The processes detailed above can additionally be improved by using one or more of the following process variants: use of antifoams use of phase transfer catalysts, use of emulsifiers, temperature in the range from 20 to 220° C., preferably 30 to 180° C., in particular 50 to 140° C., pH in the range from 0 to 11. If the reactions are carried out under superatmospheric pressure, the pressure is preferably from 1.5 to 30 bar, in particular 2 to 15 bar.

The invention furthermore relates to compounds which arise during the reaction schemes detailed above. These compounds have the formula $R-CHR^2R^3$ selected from the compounds below

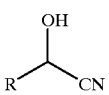  I

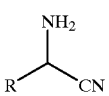  Ia

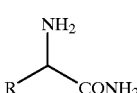  III

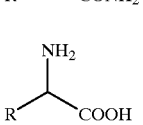  IV

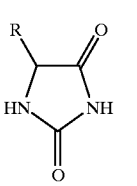  V

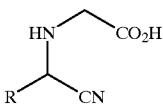  VI

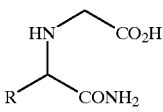  VII

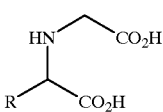  VIII

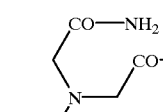  XII

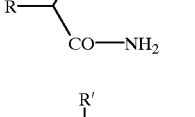

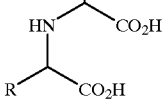  X

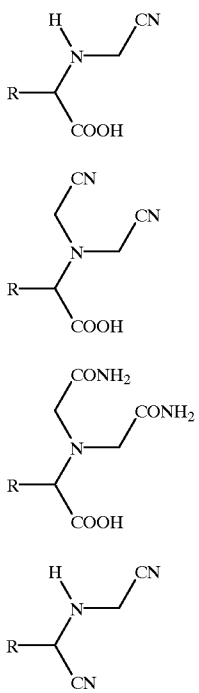

where R' is $C_{2-6}$-alkyl and R is $C_{6-20}$-alkenyl, excepting compounds of the formulae IV and V with R=$C_{17-20}$-alkenyl, of the formula I where R=n–9-decenyl and of the formula VIII where R=$C_{6-10}$-alkenyl, or R is the radical R"O—CH$_2$—CH$_2$ where R" is $C_{3-20}$-alkyl or $C_{3-20}$-alkenyl, excepting compounds of the formula IV with R"=$C_{5-20}$-alkyl and of the formula X where R"=$C_{5-8}$-alkyl.

The compounds are particularly those where R is $C_{12-20}$-alkenyl and R" is $C_{6-15}$-alkyl or $C_{3-12}$-alkenyl.

Before detailed description of the processes according to the invention, the compounds employed according to the invention are described in detail.

Suitable alkali metal, ammonium and substituted ammonium salts are, in particular, the sodium, potassium and ammonium salts, and in the case of the compounds of the formula IX, in particular the trisodium, tripotassium and triammonium salt, and organic triamine salts with a tertiary nitrogen atom.

Particularly suitable bases underlying the organic amine salts are tertiary amines such as trialkylamines having 1 to 4 carbon atoms in the alkyl, such as trimethyl- and triethylamine, and trialkanolamines having 2 or 3 carbon atoms in the alkanol residue, preferably triethanolamine, tri-n-propanolamine or triisopropanolamine.

The alkaline earth metal salts which are particularly employed are the calcium and magnesium salts.

Particularly suitable straight-chain or branched alk(en)yl radicals for the R radical are $C_6$–$C_{20}$-alkyl and -alkenyl, and of these in particular straight-chain radicals derived from saturated or unsaturated fatty acids. Examples of individual R radicals are: n-hexyl, n-heptyl, 3-heptyl (derived from 2-ethylhexanoic acid), n-octyl, isooctyl (derived from isononanoic acid), n-nonyl, n-decyl, n-undecyl, n-dodecyl, isododecyl (derived from isotridecanoic acid), n-tridecyl, n-tetradecyl, n-pentadecyl, n-hexadecyl, n-heptadecyl, n-octadecyl, n-nonadecyl, n-eicosyl and n-heptadecenyl (derived from oleic acid). Mixtures may also occur for R, in particular those derived from naturally occurring fatty acids and from synthetic industrial acids, for example those produced by the oxo synthesis.

Particularly used as $C_1$–$C_{12}$-alkylene bridges A are polymethylene groups of the formula —(CH$_2$)$_k$— where k is a number from 2 to 12, in particular from 2 to 8, ie. 1,2-ethylene, 1,3-propylene, 1,4-butylene, pentamethylene, hexamethylene, heptamethylene, octamethylene, nonamethylene, decamethylene, undecamethylene and dodecamethylene. Hexamethylene, octamethylene, 1,2-ethylene and 1,4-butylene are particularly preferred in this connection. However, it is also possible for branched $C_1$–$C_{12}$-alkylene groups to occur, for example —CH$_2$CH(CH$_3$)CH$_2$—, —CH$_2$C(CH$_3$)$_2$—CH$_2$—, —CH$_2$CH(C$_2$H$_5$)— or —CH$_2$CH(CH$_3$)—.

The $C_6$–$C_{30}$-alkyl and $C_6$–$C_{30}$-alkenyl groups may have upto 5, in particular upto 3, additional substituents of the type mentioned, and be interrupted by upto 5, in particular upto 3, nonadjacent oxygen atoms. Examples of such substituted alk(en)yl groups are —CH$_2$OH, —CH$_2$CH$_2$OH, —CH$_2$CH$_2$—O—CH$_3$, —CH$_2$CH$_2$—O—CH$_2$CH$_2$—O—CH$_3$, —CH$_2$—O—CH$_2$CH$_3$, —CH$_2$—O—CH$_2$CH$_2$—OH, —CH$_2$—CHO, —CH$_2$—OPh, —CH$_2$—COOCH$_3$ or —CH$_2$CH$_2$—COOCH$_3$.

Particularly suitable alkoxylate groups are those where m and n are each numbers from 0 to 30, especially from 0 to 15. $A^1$ and $A^2$ are groups derived from butylene oxide and, especially, from propylene oxide and from ethylene oxide. Pure ethoxylates and propoxylates are of particular interest, but ethylene oxide/propylene oxide block structures may also occur.

In the first place, process variant A which comprises two reaction routes A1 and A2 as depicted in FIG. 2 will be explained.

The long-chain α-amino nitrites of the formula IIa can be prepared from the corresponding cyanohydrins and liquid ammonia or highly concentrated aqueous ammonia solutions (concentrations from 30 to 80% by weight) or from the corresponding long-chain aldehydes, hydrogen cyanide and liquid ammonia or highly concentrated aqueous ammonia solutions. Starting materials which can be used besides pure compounds are the starting materials described in DE-A-195 18 986 from the industrial synthesis of monoaldehydes. Particularly used are mixtures of aldehydes or mixtures of aldehydes and the corresponding alcohols. In process variant A, the starting materials are preferably those from the industrial synthesis of α-amino nitrites, α-amino acids or their precursors, by which is meant the underlying cyanohydrins or the corresponding aldehydes or the hydantoins substituted in position 5. Unpurified crude material or the mother liquors produced are preferably employed.

Preferred embodiments of variant A:

Variant A

The α-amino nitrile of the formula IIa or the amino acid of the formula IV is reacted with 1.8 to 3.0 eq, in particular 2.0 to 2.5 eq, of hydrogen cyanide (HCN) and, simultaneously or sequentially, with 1.8 to 3.0 eq, in particular 2.0 to 2.5 eq, of formaldehyde in water or a mixture of water and a water-miscible organic solvent such as alcohols, ethers, etc., in particular alcohols such as methanol, ethanol, n-propanol, i-propanol, tert-butanol, with a water content of from 1 to 99%, in particular 20 to 80%, at a pH of from 0 to 11, within from 0.5 to 12 hours, in particular 1 to 5 hours. Stirring is then normally continued for from 0.5 to 20 hours, in particular 3 to 10 hours, under the reaction conditions. The cyanomethylation can in both embodiments also be carried out stepwise and with isolation of the mono (cyanomethyl) stage. It is also possible to employ glycolonitrile in place of formaldehyde and hydrogen cyanide. Hydrolysis is subsequently carried out, where appropriate after isolation of the intermediate product (XII) by filtration or decantation, normally in embodiment A2 with 2.4 to 6, in particular 3 to 5, and in embodiment A1 with 1.6 to 4, in particular 2 to 3 mole equivalents of bases able to release hydroxide ions in aqueous medium, such as alkali metal hydroxides, ammonium hydroxides, barium hydroxide, calcium hydroxide or alkali metal alcoholates, preferably aqueous sodium or potassium hydroxide solution or alcoholic sodium or potassium hydroxide solution, for example ethanolic sodium or potassium hydroxide solution, with an alcohol content of from 5 to 50%, in particular 10 to 40%, under a pressure of from 1 to 40 bar, in particular 2 to 15 bar, and from 20 to 220° C., in particular from 30 to 160° C. A particular embodiment of the hydrolysis comprises the ammonia which is produced being continuously decompressed to the set pressure through a relief valve when a preset pressure of from 1.5 and 10 bar, in particular 2 to 6 bar is reached.

The hydrophobic α-amino nitrites are obtained according to the invention either from the corresponding cyanohydrins and from 1 to 10 eq, in particular 3 to 8 eq, of liquid ammonia or 1 to 20 eq, in particular 3 to 15 eq, of a highly concentrated aqueous ammonia solution, preferably 30 to 80% strength ammonia, or directly from the underlying monoaldehydes, hydrogen cyanide and 1 to 10 eq, in particular 3 to 8 eq, of liquid ammonia or 1 to 20 eq of preferably 30 to 80% strength ammonia under a pressure of 1 to 40 bar, in particular 2 to 15 bar. Stirring is then normally continued for from 0.1 to 12 h, in particular 0.5 to 6 h, at from 0 to 35° C. under the reaction conditions. The initial temperature is preferably 0° C., which is gradually raised to 35° C.

When amino nitrites are synthesized by known methods in the case of long-chain products the resulting reaction mixtures in some cases have a very high content of the. unwanted imino dinitriles which result from the reaction between 1 molecule each of α-aminonitrile and unreacted cyanohydrin and which may cause problems in subsequent reactions. The yields of required product are then also frequently unsatisfactory and uneconomic.

Said technical improvements in the processes result in the amounts of these by-products being reduced to <5 mol % and, in the optimal case, production thereof being completely suppressed. A preferred embodiment proves to be reaction of the cyanohydrin either pure or in a suitable organic solvent, in particular alcohols, in liquid ammonia.

Hydrolysis is subsequently carried out, where appropriate after phase separation, filtration or decantation, normally with 0.8 to 2, in particular 1 to 1.5, mole equivalents of aqueous sodium or potassium hydroxide solution or alcoholic sodium or potassium hydroxide solution, for example ethanolic sodium or potassium hydroxide solution with an alcohol content of from 5 to 50%, in particular 10 to 40%, based on amino nitrile to be reacted, where appropriate under a pressure of from 1 to 40 bar, in particular 2 to 15 bar, and from 20 to 220° C., in particular 30 to 160° C.

The ammonia which is produced is continuously decompressed to the preset pressure through a relief valve when a preset pressure of from 1.5 to 10 bar, in particular 2 to 6 bar, is reached.

Alternatively, the amino nitrites can be hydrolyzed to the amino acids by saturated solution of hydrogen chloride in alcohols, in particular ethanol etc. It has proven beneficial to carry out the hydrolysis in the presence of substoichiometric amounts of alkali metal or alkaline earth metal hydroxides, in particular aqueous sodium or potassium hydroxide solution, with the addition of ketones, in particular acetone, starting the hydrolysis at temperatures <30° C. It is possible by this procedure to suppress cleavage of the amino nitrites back to the aldehyde and to optimize further the yields of amino acid. The α-amino amides initially obtained under mild reaction conditions can be either isolated and hydrolyzed further under normal hydrolysis conditions and under pressure or hydrolyzed further directly in the reaction solution after addition of appropriate amounts of aqueous alkali at elevated temperature and under superatmospheric pressure. This mechanical improvement in the process for hydrolyzing hydrophobic amino nitrites is expediently carried out in such a way that the first reaction step takes place with the addition of, preferably, 0.1 to 0.9, in particular 0.15 to 0.7, mole equivalents of alkali and 0.2 to 2, in particular 0.3 to 1, mole equivalents of the relevant ketone and from 5 to 40° C., in particular 10 to 30° C. For the further hydrolysis to the amino acids, the alkali content is increased to stoichiometric amounts, and hydrolysis is continued under superatmospheric pressure.

The amino acids employed for preparing long-chain glycine-N,N-diacetic acids can, however, also be obtained by acidic or alkaline hydrolysis under a pressure of from 1 to 40 bar of the 5-substituted hydantoins obtainable from the corresponding aldehydes, alkali metal cyanide and ammonium carbonate.

The cyanohydrins are normally prepared by known methods from the corresponding aldehyde and hydrocyanic acid with addition of bases such as triethylamine, alkali metal cyanides etc. without diluent or in the presence of a suitable organic solvent, in particular of alcohols.

The long-chain monoaldehydes employed in variants A and B are preferably derived from processes which can be carried out industrially to prepare them from easily available and low-cost basic chemicals, in particular hydroformylation reactions of corresponding α-olefins and metal-catalyzed reductions of the underlying carboxylic acids and esters. It has proven particularly advantageous to employ mixtures of aldehydes and alcohols as typically produced in a number of processes of this type. This makes it possible to dispense with addition of a water-miscible organic solvent such as methanol, ethanol, isopropanol, dioxane, etc. in the individual process steps. The alcohol which is present has not only solubilizing but also antifoam properties which may make a very advantageous contribution to reducing the unwanted foaming due to the evolution of ammonia at the hydrolysis stage. It is unnecessary to remove these alcohols from the product or the product properties. Mixtures of isomeric and homologous aldehydes as are produced in many industrial syntheses can also be reacted successfully.

The addition, according to the invention of a suitable emulsifier which is able to disperse the aldehydes, cyanohydrins, amino nitrites, amino amides or amino acids sufficiently well in the purely aqueous medium, in a concentration of 1 to 50 g/l of reaction mixture, in particular 2 to 30 g/l, results in a marked reduction in the reaction times by comparison with reaction without emulsifier. This variant of the process results in reaction times like those which can be obtained in Strecker reactions on amino nitrites or amino acids under superatmospheric pressure at elevated temperatures in an autoclave. It is particularly beneficial to carry out the reactions in the presence of an emulsifier under superatmospheric pressure. Examples of emulsifiers which can be employed successfully are sodium dodecyl sulfate, sodium dodecylbenzenesulfonate (LAS) and mixtures of hydrophobic alkyl sulfates. It is also possible to employ nonionic surfactants such as fatty alcohol ethoxylates, some of which are low-foam surfactants. The reaction times are also reduced on use of phase transfer catalysts which are able to bring about a rapid phase exchange between the hydrophobic components of aldehydes, cyanohydrins, amino nitrites, amino amides or amino acids, formaldehyde and hydrogen cyanide, and sodium cyanide in the aqueous or aqueous alcoholic system. Examples of phase transfer catalysts used are quaternary ammonium, phosphonium and other onium compounds, crown ethers and cryptands. Examples are tetraalkylammonium salts, trialkylbenzyl-ammonium salts, tetraalkylphosphonium salts and other corresponding quaternary salts.

In some variants of the processes described hereinbeforehand and hereinafter, the occurrence of foaming, in particular at the hydrolysis stage due to the ammonia which is produced, may cause problems. Addition of small or very small amounts of an antifoam, preferably a silicone antifoam, results in collapse of the foam or a reduction to a minimum which can be satisfactorily controlled industrially. It is also possible to employ other antifoam substances such as fatty alcohol ethoxylates, phosphoric esters etc. Addition of such substances is unnecessary if the reactions take place in aqueous alcoholic media, or mixtures of long-chain aldehydes and corresponding alcohols are employed. Addition of surfactants such as alcohol alkoxylates is particularly advantageous because they remain in the product after the reaction has taken place and can be employed in the mixture.

If the compounds IX result as salts, the free acids of the compounds IX can be obtained by acidification by conventional methods.

Variant B

The reaction according to the invention of iminodiacetonitrile, iminodiacetic acid or their derivatives, in particular iminodiacetic esters or iminodiacetamides, with the appropriate long-chain aldehydes and hydrogen cyanide in embodiment B takes place either by reacting crude iminodiacetonitrile or iminodiacetonitrile-containing mother liquors with the aldehyde and hydrocyanic acid to give the corresponding glycinonitrile-N,N-diacetonitrile, followed by alkaline hydrolysis to the compounds IX under a pressure of from 1 to 40 bar, in particular 2 to 15 bar, at from 20 to 220° C., in particular 50 to. 140° C., or by alkaline hydrolysis of the iminodiacetonitrile to the iminodiacetic acid and, where appropriate, its conversion into derivatives by known methods, in particular iminodiacetic esters or iminoacetamides, followed by reaction with the aldehyde and hydrocyanic acid under a pressure of from 1 to 40 bar, in particular 2 to 15 bar and from 20 to 220° C., in particular 50 to 140° C. Higher pressures are also possible, for example, by injecting protective gas such as nitrogen.

The iminodiacetonitrile is often reacted as 5 to 30% by weight mother liquor with 0.8 to 5.0 eq, in particular 1 to 3 eq, of hydrogen cyanide and, simultaneously or sequentially, with 0.8 to 3.0 eq, in particular 1.0 to 1.5 eq, of the long-chain aldehyde in water or a mixture of water and a water-miscible organic solvent, in particular alcohols, with a water content of from 1 to 99%, in particular 20 to 80%, at a pH of, preferably, 0 to 5, which is normally adjusted by adding mineral acids, within from 1 to 15 hours, in particular 2 to 6 hours, under superatmospheric pressure in an autoclave. Stirring is then normally continued for 0.5 to 20 hours, in particular 3 to 10 hours, under the reaction conditions. Hydrolysis is ultimately carried out, if appropriate after isolation of the intermediate by filtration or decantation, normally with 2 to 5, in particular 3 to 4, mol equivalents of bases able to release hydroxide ions in an aqueous medium, such as alkali metal hydroxides, ammonium hydroxides, barium hydroxide, calcium hydroxide or alkali metal alcoholates, preferably aqueous sodium or potassium hydroxide solution or alcoholic sodium or potassium hydroxide solution, in particular ethanolic sodium or potassium hydroxide solution, with an alcohol content of from 5 to 50%, in particular 10 to 40%, based on iminodiacetonitrile employed, under superatmospheric pressure. A particular embodiment of the hydrolysis consists in continuously decompressing the ammonia which is produced to the preset pressure through a relief valve when a preset pressure of from 1.5 to 10 bar, in particular 2 to 6 bar, is reached.

Variants C, D

The reaction according to the invention of unsubstituted glycine, its precursors or its secondary products cyanomethylglycine and carboxymethylglycine, which are obtainable by monosubstitution of glycine with formaldehyde and hydrogen cyanide, with the appropriate long-chain aldehydes and hydrogen cyanide in embodiments C and D is normally carried out under a pressure of from 1 to 40 bar, in particular 2 to 15 bar, from 20 to 220° C., in particular 50 to 140° C. Higher pressures are also possible, for example by injecting protective gas such as nitrogen. The pH of the aqueous or organic aqueous, in particular alcoholic aqueous, reaction medium with a water content of from 1 to 99%, in particular 20 to 80% is from 0 to 11, preferably 1 to 10. Precursors of glycine mean, for example glycinonitrile.

The formaldehyde and the hydrogen cyanide are metered simultaneously into glycine or its precursors at the stated reaction temperature and the stated pH over a period of from 0.1 to 12 hours, in particular 0.15 to 6 hours, especially 0.25 to 3 hours. Reaction is then normally allowed to continue for 1 to 20 hours, preferably 2 to 10 hours, under the reaction conditions.

In embodiment C it is expedient to employ per mol equivalent of glycine or its precursors used as starting material for the first substitution step from 1.0 to 1.05 eq of the long-chain aldehyde, preferably as technical product, and 1.0 to 1.6, in particular 1.0 to 1.4, eq of hydrogen cyanide, and for the second substitution step from 1.0 to 1.6 eq, in particular 1.0 to 1.4 eq, of formaldehyde, preferably in the form of its aqueous solution which is about 30% by weight, and from 1.0 to 1.6, in particular 1.0 to 1.4, eq of hydrogen cyanide. Normally used as starting material are aqueous solutions of glycine or its precursors with a glycine or precursor content of from 10 to 50% by weight, in particular 25 to 45% by weight.

In embodiment D it is expedient to employ per mol equivalent of the glycine or its precursors used as starting material for the first substitution step from 1.0 to 1.05 eq of formaldehyde, preferably in the form of its aqueous solution which is about 30% by weight, and from 1.0 to 1.6, in particular 1.0 to 1.4, eq of hydrogen cyanide, and for the second substitution step from 1.0 to 1.6 eq, in particular 1.0 to 1.4 eq, of the long-chain aldehyde, preferably as technical product, from 1.0 to 1.6, in particular 1.0 to 1.4, eq of hydrogen cyanide.

The hydrolysis of nitrile functionalities which are present after the reaction to give carboxylate groups is normally carried out with from 0.8 to 2.0, in particular 1.0 to 1.5, mol equivalents per nitrile functionality of aqueous sodium or potassium hydroxide solution or alcoholic sodium or potassium hydroxide solution, such as ethanolic sodium or potassium hydroxide solution with an alcohol content of from 5 to 50%, in particular under pressures from 2 to 15 bar and at from 20 to 220° C., in particular from 50 to 140° C. Higher pressures are also possible, for example by injecting protective gas such as nitrogen. It has proven to be particularly beneficial for the ammonia which is produced to be continuously decompressed to the preset pressure through a relief valve when a preset pressure of from 1 to 10 bar, in particular 2 to 6 bar, is reached.

In place of the long-chain aldehydes, formaldehyde and hydrogen cyanide, it is also possible for their synthetic equivalents, the corresponding hydrophobic cyanohydrins and glycolonitrile to be reacted in a similar way to the individual components in embodiments B, C or D.

By-products found in the particular hydrolysis solutions are occasionally small amounts of the corresponding α-hydroxy carboxylic acids and fatty acids produced on hydrolysis with unreacted cyanohydrin or the cyanohydrin formed as intermediate from aldehyde and hydrogen cyanide. Since these compounds have a beneficial effect on the properties of the product, they need not be removed from the reaction mixtures, which is why costly and elaborate purification steps are unnecessary.

Addition according to the invention of a suitable emulsifier which is able to disperse the particular long-chain aldehyde sufficiently well in the purely aqueous medium, in a concentration of from 1 to 50 g/l of reaction mixture, in particular 2 to 30 g/l, results in a marked reduction in the reaction times in embodiments B to D compared with reaction without emulsifier. This technical improvement in the process results in reaction times which are in the region of the Strecker reactions under superatmospheric pressure. Accordingly it is particularly beneficial to carry out the reactions in the presence of an emulsifier under superatmospheric pressure. Examples of emulsifiers which can be employed successfully are sodium dodecyl sulfate and mixtures of hydrophobic alkyl sulfates. The use of nonionic surfactants such as fatty alcohol ethoxylates and nonionic low-foam surfactants such as specific fatty alcohol alkoxylates or mixtures of nonionic surfactants and aldehydes equally has beneficial effects on the reaction times and yields as for variant A. These emulsifiers or surfactants may also remain in the product if required, and advantageously do not need to be removed because they may supplement or have a beneficial effect on the product properties.

The reaction times are also reduced on use of phase transfer catalysts which are able to bring about a rapid phase exchange between the long-chain aldehyde, iminodiacetonitrile and hydrogen cyanide in the aqueous or aqueous alcoholic system or between the long-chain aldehyde, glycine, its precursors or its secondary products cyanomethylglycine and carboxymethylglycine and hydrogen cyanide (variants C and D). Phase transfer catalysts which are used are described above for variant A.

The preparation process without diluent is particularly preferred, that is to say in the melt without use of additional solvents. In this case, the abovementioned emulsifiers are preferably employed. It is likewise particularly advantageous for the reaction to take place in the presence of alcohols, which may also have an emulsifying effect. The hydrolysis preferably takes place under elevated pressure, with the reaction mixture being decompressed to the required pressure if a maximum permissible pressure is exceeded. The preferred processes are explained in detail by means of examples below. The preferred alcohols are also indicated therein.

The reaction can also be carried out in accordance with the metering instructions given in DE-A-195 18 987. Further procedures can be found in WO 94/29421.

The invention is explained in detail by means of examples below.

EXAMPLES

Example 1

D,L-2-Aminotridecanonitrile 27 g (1 mol) of hydrocyanic acid are metered over the course of 30 minutes into a mixture of 190 g (1 mol) of 97% pure lauraldehyde and 12.2 g (0.12 mol) of triethylamine at 15° C. in a steel autoclave under atmospheric pressure. The mixture is then heated at 40° C. for 2 hours until aldehyde is no longer detectable in the IR spectrum. The reactor is closed, 73 g (4.3 mol) of liquid ammonia are condensed in at about 25° C. This sets up a pressure of 12 bar. The mixture is then stirred under the same conditions for 1 h before being decompressed to atmospheric pressure, the ammonia escaping. For stability reasons, the product is not worked up further but is reacted immediately. The content is determined by GC, the yield of amino nitrile determined thereby being 204 g (0.97 mol; 97% of theory).

Example 2

D,L-n-undecylalycine-N,N-diacetic acid 7.5 g (0.05 mol) of a 33% strength sodium cyanide solution are added to a solution of 59.1 g (0.25 mol) of 89% pure 2-aminotridecanonitrile from Example 1 in 150 ml of ethanol in a steel autoclave. The reactor is closed and then heated to 100° C. before simultaneously metering in 68.2 g (0.46 mol) of a 33% strength sodium cyanide solution and 51 g (0.51 mol) of a 30% strength formaldehyde solution over the course of 1 h. The mixture is stirred at the same temperature under a pressure of about 4 bar for 3 h until no further change in the cyanide content can be found by titration. After addition of 20 g (0.25 mol) of 50% strength sodium hydroxide solution, the reaction solution is hydrolyzed further at 100° C. under about 4 bar for 6 h. After cooling and decompression to atmospheric pressure, the volatile constituents are distilled off and the residue is taken up in water. The pH is then adjusted to 2 with concentrated hydrochloric acid, and the precipitate which forms is isolated by filtration. 82.6 g (0.23 mol) of 97% pure D,L-n-undecylglycinediacetic acid with a calcium binding capacity of 2.81 mmol/g are obtained, corresponding to a yield of 93% of theory.

Example 3

D,L-2-aminotridecanoic acid 6.4 g (0.11 mol) of acetone and 4 g (0.05 mol) of 50% strength sodium hydroxide solution are added successively to 105.2 g (0.25 mol) of a 50% strength solution of D,L-2-aminotridecanonitrile in ethanol at 10° C. in a steel autoclave. After warming to room temperature, the mixture is stirred for 30 minutes before being diluted with 50 ml of water, and a further 16 g (0.2 mol) of 50% strength sodium hydroxide solution are metered in. The reactor is closed and heated at 160° C. for 30 min, a pressure of about 15 bar being set up. After cooling to room temperature and decompression to atmospheric pressure, the volatile constituents are distilled off and the residue is taken up in water. The pH is then adjusted to 5 with concentrated hydrochloric acid, and the precipitate which forms is isolated by filtration. 50.3 g (0.22 mol; 88% of theory) of D,L-2-aminotridecanoic acid are obtained.

Example 4

D,L-n-undecylglycine-N,N-diacetic acid 57.3 g (0.25 mol) of 2-aminotridecanoic acid from Example 3 are added to a mixture of 250 g of water and 100 g of ethanol in a steel autoclave. 51 g (0.51 mol) of a 30% strength formaldehyde solution are added to this at room temperature under atmospheric pressure. The mixture is then stirred for 1 h, before the reactor is closed and heated to 100° C. A pressure of about 4 bar is set up and, under this, 75.7 g (0.51 mol) of a 33% strength sodium cyanide solution are metered in. The mixture is stirred further under the above conditions for 3 h until no further change in the cyanide content can be found by titration. The pH is adjusted to 13 with 50% strength sodium hydroxide solution, after which hydrolysis is continued under superatmospheric pressure for 6 h. After cooling and decompression to atmospheric pressure, the volatile constituents are distilled off and the residue is taken up in water. The pH is adjusted to 2 with concentrated hydrochloric acid, and the precipitate which forms is isolated by filtration. 83.2 g (0.23 mol) of 95% pure D,L-n-undecylglycine-N,N-diacetic acid with a calcium binding capacity of 2.75 mmol/g are obtained, corresponding to a yield of 92% of theory.

Example 5

D,L-n-undecylglycinonitrile-N,N-diacetonitrile

A suspension of 71.3 g (0.75 mol) of 99% pure iminodi-acetonitrile in 150 g of water and 100 g of methanol in a steel autoclave is adjusted to pH 1.0 with 7.5 g of 50% strength sulfuric acid. 31 g (1.14 mol) of hydrocyanic acid are added dropwise to this at room temperature, before the autoclave is closed and warmed to 35 to 40° C. 142.5 g (0.75 mol) of 97% pure lauraldehyde in 50 g of methanol are metered in by a diaphragm pump over the course of 1.5 h. The mixture is heated to 100° C. and stirred at the same temperature under a pressure of about 3.5 bar for 8 hours until no further change in the hydrocyanic acid content can be found by titration. After cooling to 10° C., the phase containing the D,L-n-undecyl-glycinonitrile-N,N-diacetonitrile which has formed is separated from the aqueous phase, and all volatile constituents are removed. Recrystallization from a little ethanol results in 192.7 g (0.67 mol; 89% of theory) of trinitrile, whose purity is determined by gas chromatography.

Example 6

D,L-n-undecylglycinonitrile-N,N-diacetonitrile

A suspension of 71.3 g (0.75 mol) of 99% pure iminodi-acetonitrile in 150 g of water and 100 g of methanol in a steel autoclave is adjusted to pH 1.0 with 7.5 g of 50% strength sulfuric acid. 23 g (0.83 mol) of hydrocyanic acid are added dropwise to this at room temperature, before the autoclave is closed and warmed to 35 to 40° C. 142.5 g (0.75 mol) of 97% pure lauraldehyde in 50 g of methanol are metered in by a diaphragm pump over the course of 1.5 h. The mixture is heated to 130° C. and stirred at the same temperature under a pressure of about 6 bar for 6 hours until no further change in the hydrocyanic acid content can be found by titration. After cooling to 10° C., the phase containing the D,L-n-undecyl-glycinonitrile-N,N-diacetonitrile which has formed is separated from the aqueous phase, and all volatile constituents are removed. Recrystallization from a little ethanol results in 197 g (0.68 mol; 91% of theory) of trinitrile, whose purity is determined by gas chromatography.

Example 7

D,L-n-undecylglycinonitrile-N,N-diacetonitrile

An emulsion of 48.0 g (0.5 mol) of 99% pure iminodi-acetonitrile and 9.0 g of sodium dodecyl sulfate in 185 g of water is adjusted to pH 1.0 with 10.6 g of 50% strength sulfuric acid. 19 g (0.7 mol) of hydrocyanic acid are added dropwise to this at room temperature, before 95 g (0.5 mol) of 97% pure lauraldehyde are metered in at 40° C. over the course of 2 hours. The mixture is heated to 70° C. and stirred at the same temperature for 6 hours until no further change in the hydrocyanic acid content can be found by titration. Phase separation starts during this reaction. After cooling to 10° C., the phase containing the trinitrile is separated from the aqueous phase and recrystallized from a little ethanol. 124 g (0.43 mol; 86% of theory) of D,L-undecylglycinonitrile are obtained, it being impossible to remove the emulsifier completely, and its yield being determined by gas chromatography.

Example 8

D,L-n-undecylplycinonitrile-N,N-diacetonitrile 48 g (0.5 mol) of 99% pure iminodiacetonitrile, 95 g (0.5 mol) of 97% pure lauraldehyde, 1.6 g of p-toluene-sulfonic acid monohydrate and 19 g (0.7 mol) of hydrocyanic acid are mixed in a flask with an efficient condenser at room temperature. The mixture is slowly heated to 70° C. and then stirred at this temperature for 3 hours until no further change in the hydrocyanic acid content can be found by titration. The crude reaction mixture is added to water, and the organic phase is separated off and recrystallized from a little ethanol. The yield of D,L-undecylglycinonitrile-N,N-diacetonitrile is 127 g (0.44 mol; 88% of theory), determined by gas chromatography.

Example 9

D,L-n-undecylglycine-N-N-diacetic acid

The partially crystalline mixture from Example 5 is introduced into 400 ml of ethanol in a steel autoclave. 536 g (2.68 mol) of 20% strength sodium hydroxide solution are added dropwise to this, and the mixture is stirred at 30° C. for 1 h. The autoclave is closed and then heated to 100° C., and hydrolysis is continued at this temperature under a pressure of about 4 bar for 6 h. After cooling to room temperature and decompression to atmospheric pressure, the volatile constituents are distilled off and the residue is taken up in water. The pH is adjusted to 2 with concentrated hydrochloric acid, and the precipitate which forms is isolated by filtration. 231 g (0.64 mol) of 95% pure D,L-n-undecylglycinediacetic acid with a calcium binding capacity of 2.75 mmol/g are obtained, corresponding to a yield of 96% of theory (85% of theory based on iminodiacetonitrile).

It is also possible to employ mixtures from Examples 6, 7 or 8 in place of the mixture from Example 5.

We claim:

1. A process for preparing compounds of the formula IIb:

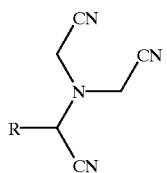

(IIb)

wherein

R is $C_6$–$C_{30}$-alkyl or $C_6$–$C_{30}$-alkenyl, which may additionally have up to 5 hydroxyl groups, formyl groups, $C_1$–$C_4$-alkoxy groups, phenoxy groups or $C_1$–$C_4$-alkoxycarbonyl groups as substituents and may be interrupted by up to 5 nonadjacent oxygen atoms, or alkoxylate groups of the formula —$(CH_2)_k$—O—$(A^1O)_m$—$(A^2O)_n$—Y, wherein $A^1$ and $A^2$ are, independently of one another, 1,2-alkylene groups having 2 to 4 carbon atoms, Y is hydrogen, $C_1$–$C_{12}$-alkyl, phenyl or $C_1$–$C_4$-alkoxycarbonyl, and k is 1, 2 or 3, and m and n are each numbers ranging from 0 to 50, and the total of m+n must be at least 4, comprising:

reacting iminodiacetonitrile with an aldehyde of the formula R—CHO and HCN or an alkali metal cyanide, wherein the process is conducted (a) in the absence of an organic solvent by reacting without diluent and in the presence of a Lewis or Brönsted acid, or (b) in the presence or absence of an organic solvent and in the presence of an emulsifier, or (c) in the presence or absence of an organic solvent and under a pressure in the range from 2 to 15 bar.

2. A process for preparing compounds of the of the formula IIb:

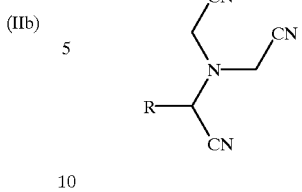

(IIb)

wherein

R is $C_6$–$C_{30}$-alkyl or $C_6$–$C_{30}$-alkenyl, which may additionally have up to 5 hydroxyl groups, formyl groups, $C_1$–$C_4$-alkoxy groups, phenoxy groups or $C_1$–$C_4$-alkoxycarbonyl groups as substituents and may be interrupted by up to 5 nonadjacent oxygen atoms, or alkoxylate groups of the formula $(CH_2)_k$—O—$(A^1O)_m$—$(A^2O)_n$—Y, wherein $A^1$ and $A^2$ are, independently of one another, 1,2-alkylene groups having 2 to 4 carbon atoms, Y is hydrogen, $C_1$–$C_{12}$-alkyl, phenyl or $C_1$–$C_4$-alkoxycarbonyl, and k is 1, 2 or 3, and m and n are each numbers from 0 to 50, and the total of m+n must be at least 4, comprising:

reacting a compound of the formula IIa:

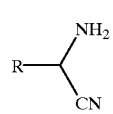

(IIa)

with formaldehyde and HCN or an alkali metal cyanide, wherein the process is carried out in the presence or absence of a solvent under a pressure in the range from 1 to 40 bar.

* * * * *